US00PP30549P3

(12) United States Plant Patent
Zhang

(10) Patent No.: US PP30,549 P3
(45) Date of Patent: Jun. 4, 2019

(54) KIWI PLANT NAMED 'HFY01'

(50) Latin Name: ***Actinidia chinensis* pl**
Varietal Denomination: HFY01

(71) Applicant: Sichuan Hua Sheng Agriculture Co., Ltd., Chengdu (CN)

(72) Inventor: Li Ming Zhang, Chengdu (CN)

(73) Assignee: Sichuan Hua Sheng Agriculture Co., Ltd., Chengdu (CN)

( * ) Notice: Subject to any disclaimer, the term of this patent is extended or adjusted under 35 U.S.C. 154(b) by 0 days.

(21) Appl. No.: 15/530,986

(22) Filed: Apr. 4, 2017

(65) Prior Publication Data

US 2017/0295680 P1 Oct. 12, 2017

(30) Foreign Application Priority Data

Apr. 6, 2016 (QZ) ..... PBR 2016/0898

(51) Int. Cl.
*A01H 5/08* (2018.01)

(52) U.S. Cl.
USPC ..... Plt./156
CPC ..... *A01H 5/08* (2013.01)

(58) Field of Classification Search
USPC ..... Plt./156
See application file for complete search history.

*Primary Examiner* — Anne Marie Grunberg
(74) *Attorney, Agent, or Firm* — Foley & Lardner LLP

(57) ABSTRACT

A new and distinct *Actinidia* plant named 'HFY01', particularly characterized by its strong growth habit, end-April time to bloom and end of October time to harvest, fruit size and shape, and resistance to *Pseudomonas syringae* pv. *actinidiae*.

4 Drawing Sheets

Latin name of the genus and species of the plant claimed: *Actinidia chinensis* pl.

Variety denomination: 'HFY01'.

BACKGROUND OF THE INVENTION

The present invention relates to a new and distinct cultivar of *Actinidia* plant, botanically known as *Actinidia chinensis* pl of the Actinidiacea family, and hereinafter referred to by the variety denomination 'HFY01'.

The new *Actinidia* cultivar is a product of a controlled breeding and pollination program conducted by the inventor, in Xia Yuan Village, Shifang county, Sichuan Province, China. The objective of the breeding and pollination program was to develop a new *Actinidia* cultivar with a dark yellow fruit flesh color.

The new *Actinidia* cultivar originated from a open pollination made by the inventor(s) in Xia Yuan Village, Shifang County, Sichuan province, China. The female or seed parent is the *Actinidia chinensis* pl. cultivar designated JXFX-CK-04136, which was discovered as a seed collected from trees growing in the wild in Fengxin county, Jiangxi province, China, in 2004 and subsequently grown in a cultivated area. The variety was developed through open pollination and the male or pollen parent is not known.

Seeds that produced the female parent JXFX-CK-04136 were sown in February 2005 and 300 seedlings were then planted out in a field in Shifang County, Sichuan Province, China in February 2005. The plants were pollinated through open pollination of a mix of *Actinida chinensis* pl. and the male or pollen parent is not known. The seedlings first fruited in in April 2008. A total of 1 female seedlings were propagated by graft in October 2009. The new *Actinidia* cultivar was selected by the inventor(s) in a controlled environment in 2010 in Shifang County, Sichuan Province, China.

Asexual reproduction of the new *Actinidia* cultivar by grafting on to rootstocks of *Actinidia deliciosa* pl. was first performed in April 2012 in a kiwifruit research station in Shifang county Sichuan province, China, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'HFY01' which in combination distinguish this *Actinidia* as a new and distinct cultivar:

1. Very strong growth habit. In soil of PH 5-6.5 and annual average temperature of 16-18° C., the claimed variety will fruit in the second year after grafting and can produce up to 20-30 t/ha of fruit by the fourth year of fruiting.
2. Flowering time and blooming period. Flowering time is in about end-April in Sichuan Province, China and the blooming period is about 5 to 8 days.
3. Harvesting time. The harvesting time is in early-December in Sichuan Province, China.
4. Fruit Shape and Size. The general fruit shape is long-trapezium with a weakly depressed stylar end. The average fruit weight is 85 g and maximum fruit weight is 120 g;
5. Pest resistance. The claimed variety shows strong resistance to *Pseudomonas syringae* pv. *actinidiae* (PSA).

In comparison to the parental variety, 'JXFX-CK-04136' (unpatented), 'HFY01' differs primarily in the traits listed in Table 1.

TABLE 1

| Trait | New Cultivar 'HFY01' | Female Parent 'JXFX-CK-04136' | Male Parent Open pollen |
|---|---|---|---|
| flavor | sweet | acid | No fruit |
| Average fruit weight | 85 g | 60 g | No fruit |
| Fruit shape | long- trapezium | elliptic | No fruit |
| Color of flesh | Dark yellow | Green yellow | No fruit |
| shape of core | triangle | circular | No fruit |
| General shape of stylar end | Slightly depressed | Deeply depressed | No fruit |
| Plant resistance | More resistance | Less resistance | |

Of the many commercial varieties known to the present inventor(s), the most similar in comparison to the new *Actinidia* cultivar 'HFY01' is the variety 'Jing Feng' (unpatented), in the following characteristics

TABLE 2

| Characteristic | New Cultivar 'HFY01' | Comparison Cultivar 'Jing Feng' |
|---|---|---|
| Average fruit weight | 85 g | 90 g |
| Fruit shape | long- trapezium | elliptic. |
| General shape of stylar end | Slightly depressed | Weekly blunt protruding |
| Color of inner pericarp (locules) | dark Yellow | medium yellow |
| general shape of core in cross section | triangle | transverse elliptic |
| young leaf petioles anthocyanin coloration | strong. | week |
| Plant resistance | More resistance | Less resistance |
| Sugar content (at picking time): | 17 to 18 Brix fruit sweetness is very hight | 13 to 14 Brix Fruit sweetness is very low, |
| Acidity/Starch (at picking time) | 1 to 1.4 g/lt Fruit acidity is low | 1.5-2.0 g/lt Fruit acidity is high |

BRIEF DESCRIPTION OF THE DRAWINGS

The accompanying photographs illustrate the overall appearance of the new *Actinidia* cultivar 'HFY01' showing the colors as true as is reasonably possible with colored reproductions of this type. Colors in the photographs may differ slightly from the color values cited in the detailed botanical description, which accurately describe the color of 'HFY01'. Plant parts shown in the photographs are from approximately 4 year old plants.

DETAILED BOTANICAL DESCRIPTION

Figure 1:
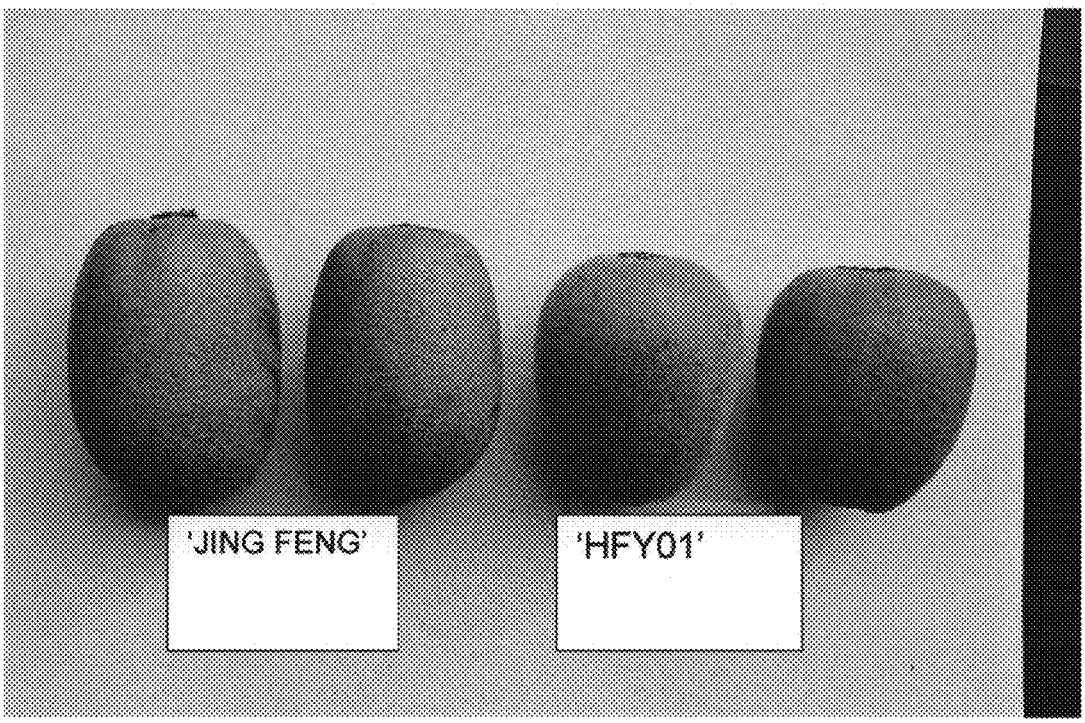
FIG. 1. Shows typical whole fruit of the comparison variety 'JING FENG' (left) compared to typical whole fruit of the claimed variety 'HFY01' (right).
Figure 2:
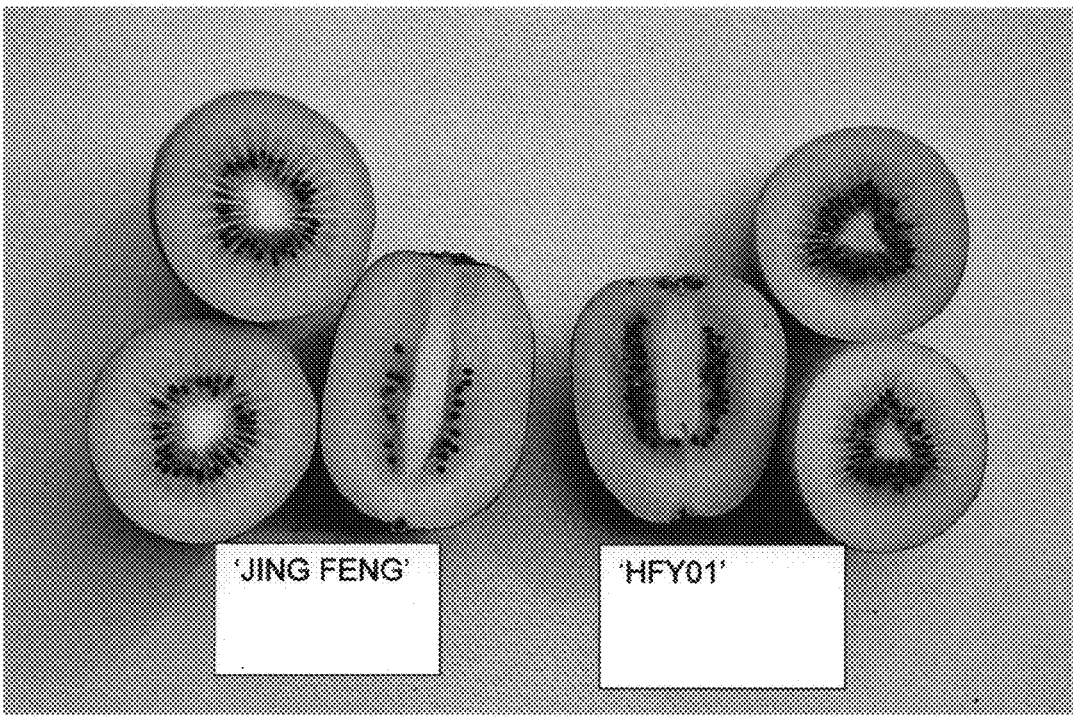
FIG. 2. Shows a cross-sectional view of typical whole fruit of the comparison variety 'JING FENG' (left) compared to typical whole fruit of the claimed variety 'HFY01' (right).
Figure 3A:
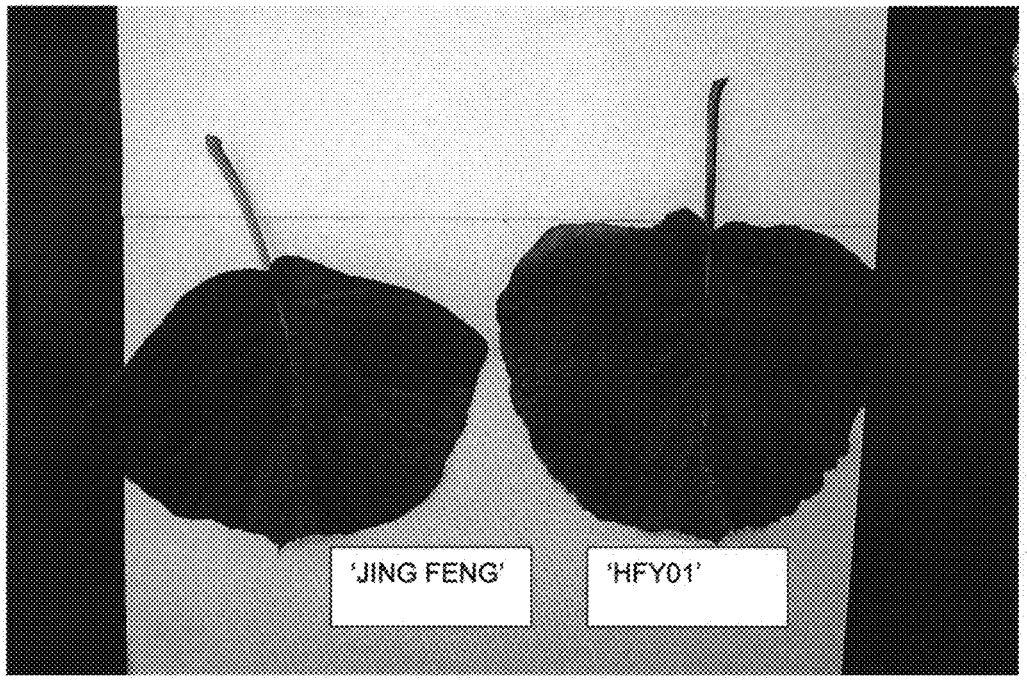
FIG. 3A. Shows the upper side of a typical leaf of the comparison variety 'JING FENG' (left) compared to a typical leaf of the claimed variety 'HFY01' (right).
Figure 3B:
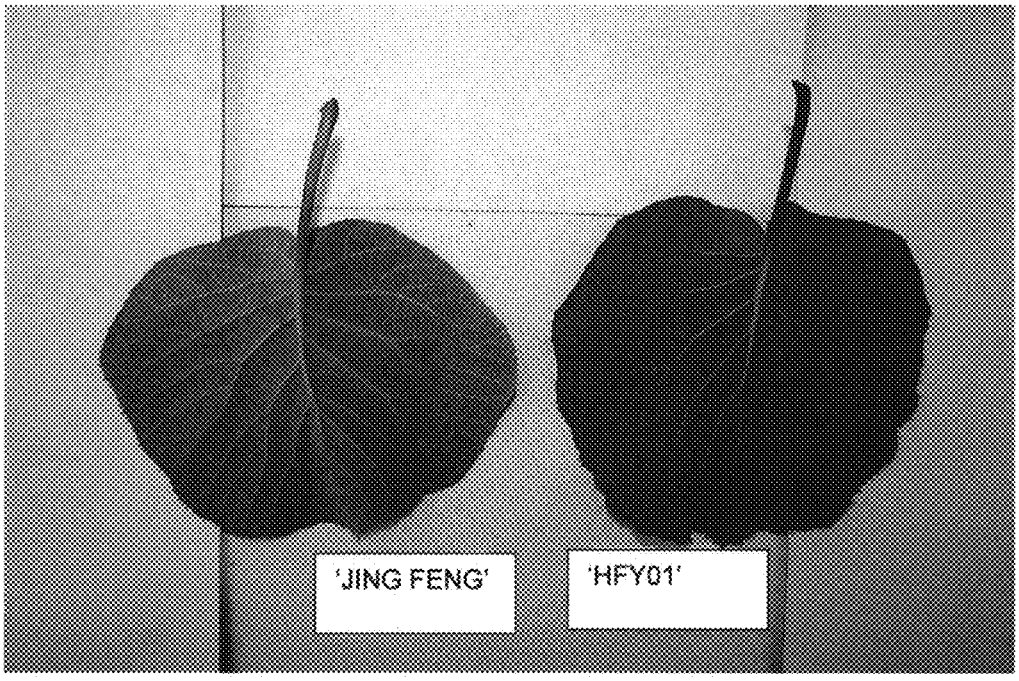
FIG. 3B. Shows the under side of a typical leaf of the comparison variety 'JING FENG' (left) compared to a typical leaf of the claimed variety 'HFY01' (right).
Figure 4A:
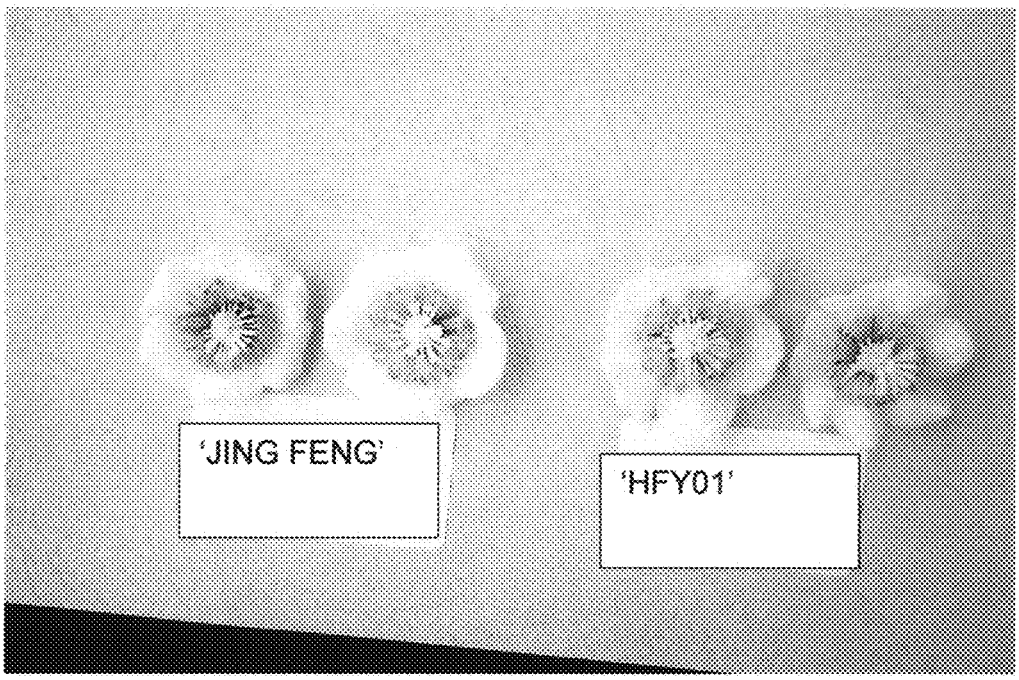
FIG. 4A. Shows the upper side of typical flowers of the comparison variety 'JING FENG' (left) compared to typical flowers of the claimed variety 'HFY01' (right).
Figure 4B:
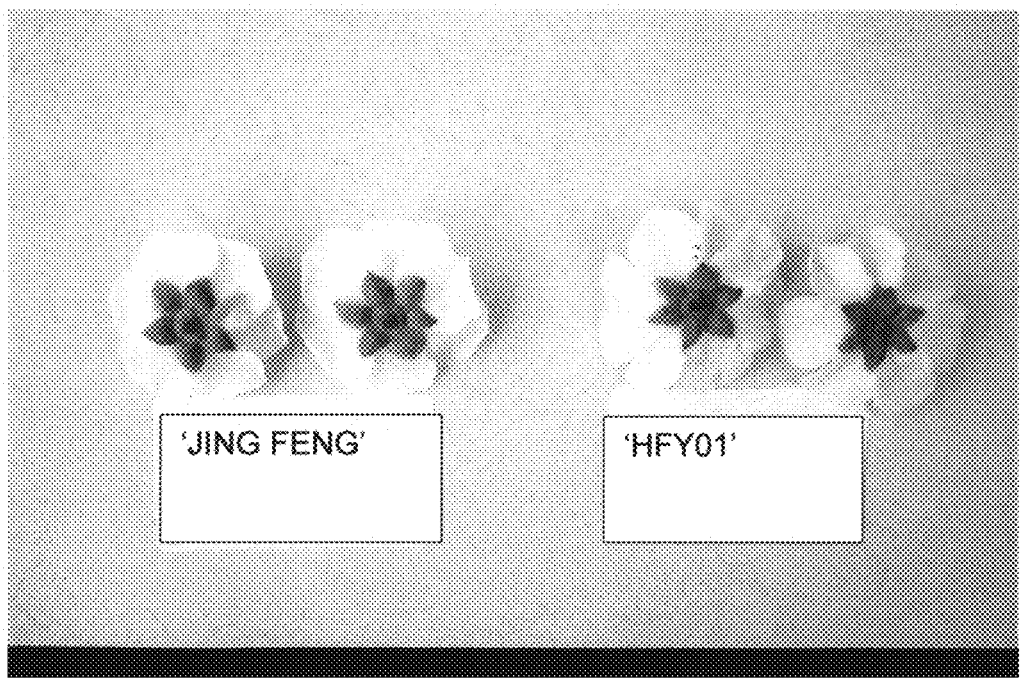
FIG. 4B. Shows the under side of typical flowers of the comparison variety 'JING FENG' (left) compared to typical flowers of the claimed variety 'HFY01' (right).

The new *Actinidia* cultivar 'HFY01' has not been observed under all possible environmental conditions. The phenotype of the new cultivar may vary with variations in environment such as temperature, light intensity, and day length without any change in the genotype of the *Actinidia*.

The aforementioned photographs, together with the following observations, measurements and values describe plants of 'HFY01' as grown outside in a field in Shifang county, Sichuan Province, China, under conditions which closely approximate those generally used in commercial practice.

Unless otherwise stated, the detailed botanical description includes observations, measurements and values based on 4 year old 'HFY01' plants grown in the field in Shifang county, Sichuan Province, China from 2009 to 2013. Quantified measurements are expressed as an average of measurements taken from a number of plants of 'HFY01'. The measurements of any individual plant, or any group of plants, of the new cultivar may vary from the stated average.

Color references are made to The Royal Horticultural Society Colour Chart (R.H.S.), $4^{th}$ Edition, except where general colors of ordinary significance are used. Color values were taken under daylight conditions at approximately 10:00AM in Shifang county, Sichuan Province, China.

All of the plants of 'HFY01', insofar as they have been observed, have been identical in all the characteristics described below.

Classification:

*Botanical.*—*Actinidia chinensis* pl.

*Commercial.*—'HFY01'.

*Common.*—Kiwifruit, kiwi, Chinese gooseberry, Yangtao.

Parentage:

*Female or seed parent.*—*Actinidia* cultivar designated 'JXFX-CK04136' (unpatented).

*Male or pollen parent.*—Open Pollination.

Propagation: Grafting on to rootstocks of *Actinidia deliciosa* C. F Liang.

Growing conditions:

*Light intensities.*—Full sunlight or slight shade.

*Temperature.*—During day, grown in range of 16° C. to 37° C., and during evening, grown in range of 10° C. to 28° C. Avoid frost injury.

*Irrigation.*—Amble irrigation during growing season with good drainage.

*Fertilization.*—Plants prefer and thrive in soil rich in organic matter. Heavy nitrogen feeders during the first half of growing season.

*pH.*—5.0 to 6.5.

*Growth regulators.*—No use.

*Pruning or trimming requirements.*—For best fruit production, "cane replacement" pruning during the winter season when plant is dormant. Pruned plants will remain more compact and bear larger fruit.

Plant:

*Sex expression*.—Female.

*Age*.—Observed plants were 4 years old.

*Vigor*.—Vigorous growth.

*Habit*.—Woody, twining vine (liana), supported by fence system.

*Size at maturity* (*area covered by one plant*).—Length: Typical: About 3 m to 4 m. Observed: About 4 m to 5 m. Width: Typical: About 2 m to 3 m. Observed: About 3 m to 4 m. Height: Typical: About 2 m to 3 m. Observed: About 2 m to 3 m.

*Stem*.—Length: About 2 m to 5 m. Diameter: About 8 mm to 15 mm. Surface texture: Upper surface: downy. Lower surface: downy. Pith: present; pith type is hollow. Pubescence (upper/lower surface): downy and aparese RHS 163A. Bark Color: Upper surface: RHS 199A. Lower surface: RHS 199C.

*Young shoot*.—Length: Varies due to shape of plant; maximum of 3 m to 6 m; minimum of 30 cm/m to 60 cm/m. Diameter: About 5 mm to 30 mm. Surface texture: Upper surface: downy. Lower surface: downy. Pubescence: present. Color: RHS 199B. Upper surface: downy. Lower surface: downy. Color: RHS 199C. Anthocyanin coloration of the growing tip: RHS 124B.

*Mature laterals*.—Length: Varies due to shape of plant; maximum of 3 m to 6 m; minimum of 0.5 cm/m to 3.0 cm/m. Diameter: About 5 mm to 30 mm. Surface texture: Upper surface: smooth. Lower surface: smooth. Pubescence: absent. Color: Upper surface: RHS 199B. Lower surface: RHS 199B.

*Lenticels*.—Length: About 0.2 mm to 0.5 mm. Width: About 0.2 mm to 0.5 mm. Color: RHS 155D. Density: About 1 to 2/cm$^2$.

*Buds*.—Shape: ellipsoid. Length: About 0.6. Width: About 0.4. Color: Apex, RHS 23C, and base, RHS 34A. Texture: deep. Pubescence: absent. Color RHS 23C.

*Leaf scar*.—Shallow.

*Leaves* (*mature*).—Arrangement and Aspect: touching each other. Size: Length: About 110 mm. Width: About 120 mm. Overall Shape: ovate.

*Apex shape*.—Acuminate. Base shape: rounded. Distance between basal leaf lobes: About 50 mm.

*Leaf blade*.—

*Shape of apex*.—Rounded. Color: Upper surface: RHS 134A. Under surface: RHS 134C. Pubescence: none. Puckering/blistering: Upper surface: weak. Lower surface: weak. Glaucosity: Upper surface: absent. Lower surface: absent. Venation: Type: feather shaped venation from central vein to the leaf edge. Color: RHS 132B.

*Leaf axil*.—Color: RHS 132B. Anthocyanin coloration: RHS 132B.

*Petiole*.—Length: About 90 mm. Diameter: About 2 mm. Texture: sparsely pubescent. Pubescence: very sparse to absent. Color: RHS 131B. Anthocyanin coloration (upper surface): RHS 131C.

*Stipule*.—None.

Inflorescence:

*Blooming time*.—Full bloom on or about April 25 in Sichuan Province, China.

*Blooming period*.—About 7 to 9 days.

*Fragrance*.—Typical of kiwifruit flower.

*Type*.—Cyme.

*Number of flowers per inflorescence*.—About 3.

*Inflorescence size* (*terminal or king*).—Diameter: About 4 cm. Depth: About 4.5 cm.

*Petals*.—Arrangement: overlapping. Mean number per flower: range of 5 to 6. Size: Length: About 35 mm. Width: About 30 mm. Length/width ratio: 1:1.2. Overall shape: ovate. Apex shape: acute. Base shape: flat. Texture (upper surface): weak. Texture (lower surface): weak. Margin: (please describe). Color (upper surface): Apex, RHS 155C, and base, RHS 155C. Color (lower surface): Apex, RHS 155D, and base, RHS 155D.

*Sepals*.—Arrangement: overlapping. Mean number per flower: range of 5 to 6. Size: Length: About 20 mm. Width: About 15 mm. Length/width ratio: 1:3. Overall shape: ovate. Apex shape: acuminate. Base shape: flat. Texture (upper surface): weak. Texture (lower surface): weak. Color (upper surface): Apex, RHS 132B and base, RHS 132B. Color (lower surface): Apex, RHS 132C and base, RHS 132C.

*Pedicel*.—Length: About 40 mm. Diameter: About 0.2 mm. Texture: smooth. Color: RHS 131C.

Reproductive organs:

*Androecium*.—None; Stamen, Anthers, Filaments and Pollen not present. Pollination Requirements: Almost all *Actinidia* species are dioecious, so female cultivars must be interplanted with male pollinizers to ensure fruit production on the female cultivar.

*Gynoecium*.—Pistils: Quantity: 36. Length: About 1 mm. Color: RHS 155D. Styles: Length: About 2 mm. Width: About 1.5 mm. Attitude: erect. Stigmas: Length: About 3 mm. Width: About 2 mm. Ovary: Shape: ovoid. Length: About 3 mm. Width: About 2 mm. Pubescence: none.

Fruit:

*Keeping quality*.—The fruit can be stored in cold temperature conditions for up to 6 months without losing firmness and juiciness. It has a shelf life up to 2 weeks without losing firmness and juiciness.

*Maturity when described*.—Harvest time is about the end of October in Sichuan Province, China. Fruit is ripe for eating at harvest.

*Firmness*.—About 5-7 kg/cm$^2$.

*Maturity period after full bloom*.—About 170-180 days after full bloom around April 25$^{th}$.

*Type*.—Berry.

*Average fruit weight and size*.—Weight: About 85 g. Height: About 55 mm. Diameter (at widest point): About 49 mm. Diameter (at narrowest point): About 47 mm.

*Fruit shape*.—General shape: long-trapezium. Styler end description: weakly depressed. Shoulder shape of stalk end: rounded. Cross-section shape at median: transverse elliptic.

*Skin*.—Firmness (at picking time): 4 to 5 kg/cm$^2$. Texture: smooth; lenticels are inconspicuous. Pubescence: none. Color: At harvest: RHS 164B. During ripening: RHS 164B. At maturity for consumption: RHS 164B.

*Flesh* (*at maturity for consumption*).—Texture: tender and juicy. Aroma: good. Sugar content (at picking time): 17 to 18 Brix. Acidity/Starch (at picking time) 1 to 1.4 g/lt. Outer pericarp: Color: RHS 17A. Inner pericarp (locules): Number (per fruit): About 45. Shape: oblong. Length: About 55 mm. Width: About 40 mm. Color: RHS 17B. Core: Shape and symmetry: triangle. Diameter (maximum): About 8 mm. Diameter (minimum): About 5 mm. Woody spike: absent. Color: RHS 155A.

Seeds:

*Number per fruit*.—About 1500-2000.

*Shape*.—Cylindrical.

*Length*.—About 1 mm.

*Width*.—About 0.5 mm.

*Texture*.—Striped, smooth.

*Color at maturity* (*in flesh*).—RHS 183A.

*Color at maturity* (*when dried*).—RHS 164A.

Cultivar use: Fresh market.

Disease/pest resistance: Resistance to *Pseudomonas syringae* pv. *actinidiae* (PSA) is stronger than the known kiwi varieties 'JINGFEN', 'HOR16A', and 'HONGYANG'.

Disease/pest susceptibility: Some susceptibility to *Pseudaulacaspis pentagona* (White Peach Scale); *Adoxophyes orana* Fisher (Summer fruit tortrix); *Acleris fimbriana* Thunberg (Yellow Tortrix Moth); and *Anomala corpulenta* Motsch. (Scarabaeidae).

Winter hardiness: Tolerant to temperatures down to −5° C. without observed damage to wood and buds of dormant *Actinidia* plants; but open flowers and young fruitlets are killed by exposure to 5° C., depending on the length of exposure.

Drought/heat tolerance: Tolerant to temperatures up to 35° C., growth is limited by drought periods without irrigation.

Events:

*Time of vegetative budbreak*.—Mid-February in Sichuan Province, China.

*Time of beginning of flowering*.—End-April in Sichuan Province, China.

*Time of maturity for harvest*.—End of October in Sichuan Province, China.

I claim:

1. A new and distinct *Actinidia chinensis* Pl. plant named 'HFY01', as illustrated and described herein.

* * * * *